United States Patent [19]

Van Der Zel

[11] Patent Number: 5,266,030
[45] Date of Patent: Nov. 30, 1993

[54] METHOD FOR MANUFACTURING A DENTAL PROSTHESIS

[75] Inventor: Joseph M. Van Der Zel, Zwaag, Netherlands

[73] Assignee: Elephant Holding B.V., Le Hoorn, Netherlands

[21] Appl. No.: 40,892

[22] Filed: Mar. 31, 1993

[30] Foreign Application Priority Data

Apr. 6, 1992 [NL] Netherlands .............. 9200642

[51] Int. Cl.$^5$ ............................... A61C 19/04
[52] U.S. Cl. ................................... 433/68; 433/214; 433/215; 433/223
[58] Field of Search ............... 433/69, 213, 214, 215, 433/223

[56] References Cited

U.S. PATENT DOCUMENTS 4,411,626 10/1983 Becker et al. .................. 433/223
4,478,580 10/1984 Barrut .................................. 433/223
4,575,805 3/1986 Moermann et al. ............ 433/204
4,837,732 6/1989 Brandestini et al. ............ 433/223

Primary Examiner—John J. Wilson
Attorney, Agent, or Firm—Curtis, Morris & Safford

[57] ABSTRACT

A method for manufacturing a dental prosthesis, wherein the shape of the prepared part of the teeth in question is established by scanning at least a part of the teeth, or a replica thereof, by means of a three-dimensional scanner. In order to be able to determine the desired shape of the prosthesis, it is not only necessary to know the shape of the part of the teeth in question, but also the circumferential edge of the preparation, i.e. the part of the teeth that has been prepared for receiving the dental prosthesis. The preparation line is made visible for the scanner by providing the teeth at one side of this preparation line with a coating which the scanner is capable of recognizing.

14 Claims, 2 Drawing Sheets

METHOD FOR MANUFACTURING A DENTAL PROSTHESIS

FIELD OF THE INVENTION

The invention relates to the manufacturing of a dental prosthesis, wherein the shape of the prepared part of the teeth in question is established by scanning at least a part of the teeth, or a replica thereof, by means of a three-dimensional scanner. The part of the teeth to be covered with the prosthesis is bounded by a preparation line, which forms the boundary with the non-prepared part of the teeth. Such a method is known from U.S. Pat. No. 4,575,805.

BACKGROUND OF THE INVENTION

The expression "teeth" in this specification is used for parts of the inside of the mouth which includes one or more teeth and surrounding tissues.

A part of the teeth on which a prosthesis, for example a dental crown, an inlay, a veneer (facet) or a bridge is to be fitted, is suitably trimmed or prepared for that purpose. The dental crown will be fitted on the prepared part of the teeth, for example a molar. For that purpose the inner surface of the dental crown must correspond with the shape of the prepared part of the teeth, taking into account, of course, the bonding agent (cement) to be applied. In order to determine the shape of the inner surface of the prosthesis the shape of the prepared part of the teeth may be established by means of a three-dimensional scanner, which scans the respective part of the teeth. Such a scanner scans the surface in question with, for example, a helium-neon laser beam or an infrared light beam. The reflection of the laser or infrared light beam on the surface can be detected by a so-called CCD (Charged Coupled Device) video camera, after which the detection is digitized and recorded.

It is not unusual to make a replica, made of plaster for example, of the part of the teeth or of the whole set of teeth first. In that case the scanning of the part of the teeth in question may be carried out on the replica. One advantage of using a replica is that a replica is easier for access by the scanner than the teeth themselves.

The prepared part of the teeth blends with a non-prepared part of the teeth, which will not be covered by the prosthesis. This transition—between the prepared part and the non-prepared part—is called the preparation line. In case of a dental crown this line runs around a tooth, generally near the implantation in the jaw.

In principle the preparation line can be perceived as an edge present on the surface of the teeth when scanning the shape of the part of the teeth. Practical tests, however, have shown that it is not possible to determine the preparation line in a sufficiently reliable manner on the basis of the scanner detections. That is why a method has been developed to display the surface detected by the scanner on a screen in such a manner, that the preparation line becomes visually recognizable. After that the preparation line can be established manually and be recorded in the scanner (or computer) memory by moving a pointer across the screen—along the preparation line—by means of a mouse.

OBJECTS OF THE INVENTION

The object of the invention is to provide a method, wherein the three-dimensional scanner completely establishes the entire inner surface of the prosthesis to be placed, including the location of the preparation line.

SUMMARY OF THE INVENTION

In order to accomplish that objective a part of the teeth, or the replica thereof, is, according to the invention, provided—at one side of the preparation line—with a coating which the scanner is capable of recognizing, so that the scanner establishes the location of the preparation line.

According to the invention it is preferred to apply the coating on the part of the teeth which is not going to be covered by the prosthesis itself, or on the corresponding part of the replica, as the case may be.

Dependent on the type of scanner being used, certain substances can be used for the coating. According to the invention it is preferred to use a coating which includes a colorant, so that the coating is also clearly visible.

When use is made of a scanner which detects the surface of the shape to be scanned by means of reflection of a light (laser) beam or an infrared beam, use is preferably made according to the invention of a coating containing a substance which absorbs the beam. According to a preferred embodiment of the invention this substance is preferably a black colorant.

In order to more fully explain the invention a number of embodiments will be described in more detail hereafter with reference to the drawing.

BRIEF DESCRIPTION OF THE DRAWINGS

Corresponding parts are numbered alike in the various Figures.

DETAILED DESCRIPTION OF A PREFERRED EMBODIMENT

Figure 1:
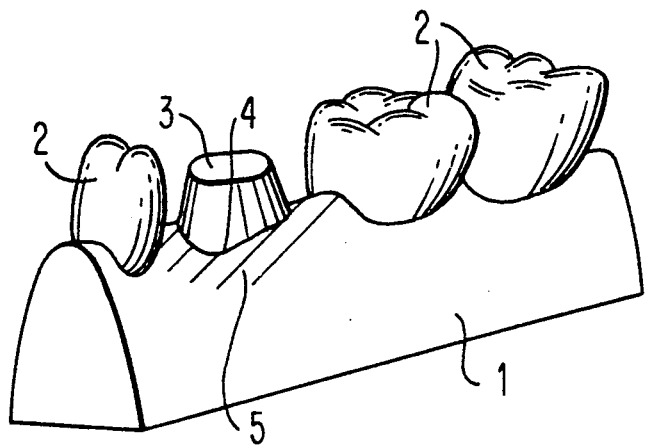
FIG. 1 is a perspective view of a part of the teeth which has been prepared for a dental crown to be fitted.

FIG. 1 shows a part 1 of a set of teeth, or of a replica thereof, comprising three teeth 2 and a dental element 3 located therebetween, which has been prepared for a dental crown (not shown) to be fitted thereon. The dental crown when installed will cover the prepared part of the dental element 3 up to the preparation line 4.

In order to be able to form the inner side of the dental crown into the correct shape it is necessary to determine the shape of the prepared dental element 3 first. This is done by means of a three-dimensional scanner, such as for example described in the aforesaid U.S. Pat. No. 4,575,805. The scanner scans the surface of the part of the teeth adjacent to the dental element 3, as well as the dental element 3 itself.

In order to be able to manufacture the dental crown it is not only required to establish the shape of the dental element 3, but it is also necessary to establish where the preparation line 4 is located, i.e. the point where the prepared part of the dental element 3 blends with the rest of the teeth. The scanner will perceive this to be an edge, but in practice this edge, as regards shape, constitutes an insufficiently distinct marking for unequivocal detection by the scanner.

In order to ensure that the scanner will recognize the preparation line, a part 5 of the teeth, represented by the hatched area in FIG. 1, has been coated with a black colorant, which does not reflect the scanner beam but which on the contrary absorbs it. The colorant is applied by hand on the part 5 of the teeth up to the preparation line 4, which is a relatively simple operation.

As being applied the scanner exactly detects the surface which is to be covered by the dental crown. The use of the colorant also provides an adequate visual image of the shape.

Figure 2:
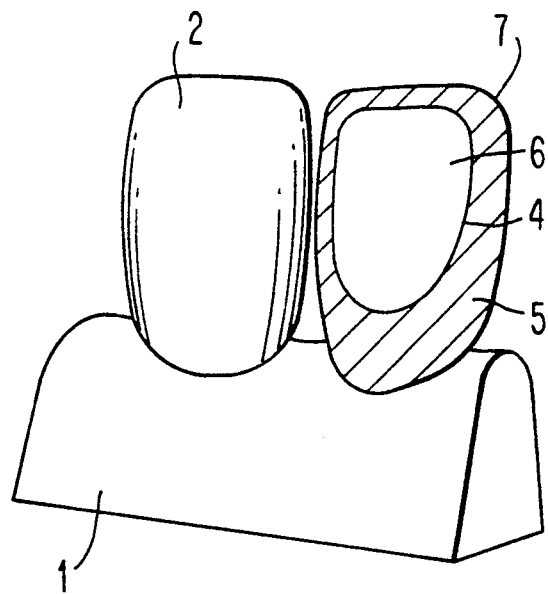
FIG. 2 is an elevational view, partly in section, of a part of the teeth which has been prepared for a facet to be fitted.

FIG. 2 shows a part of the teeth with a tooth 2 and a tooth 7 having a prepared surface 6, bounded by the preparation line 4. The surface 6 has been prepared for being covered by a facet. The hatched area 5 of tooth 7 has been coated with a substance which is detected by a scanner, for example a black colorant which absorbs the scanner beam.

Figure 3:
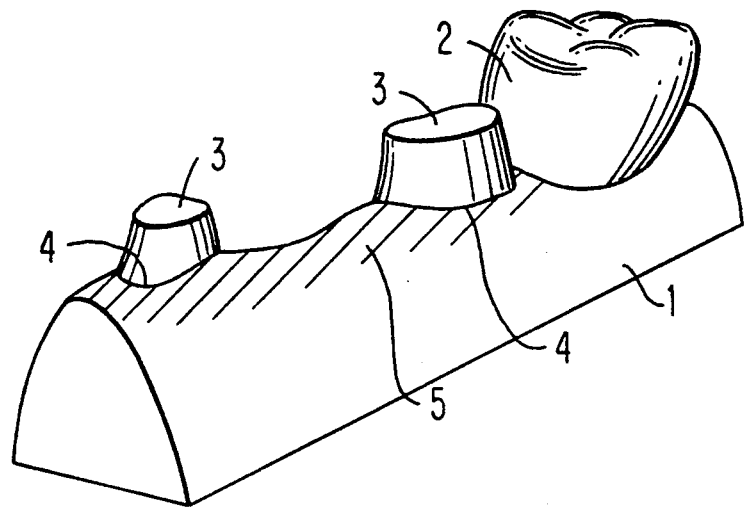
FIG. 3 is a perspective view of a part of the teeth which has been prepared for a bridge to be fitted.

FIG. 3 shows an example wherein a bridge will be fitted on the prepared teeth 3. The hatched area 5 up to the preparation line 4 is coated with a black colorant.

Figure 4:
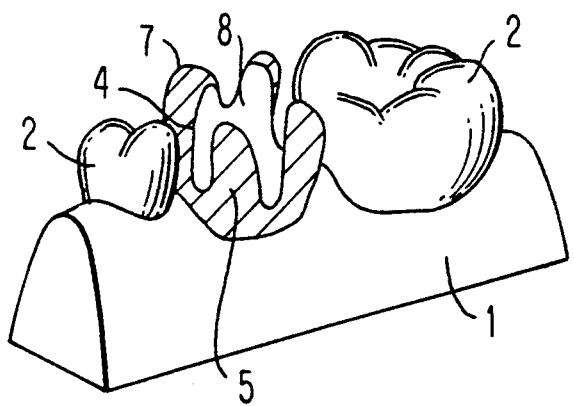
FIG. 4 is a perspective view of a part of the teeth which has been prepared for an inlay to be fitted.

FIG. 4 shows a tooth 7 located between two teeth 2, with tooth 7 having been prepared for an inlay to be fitted. The inlay will be fitted in the space 8 within the tooth 7. The area 5 of the tooth 7 which will not be covered by the inlay is shown as a hatched area, with the hatching indicating the location of the black colorant.

Of course the relevant part 5 of the teeth may also be coated with another substance which the scanner can recognize, a colored substance is preferred, however, because it can readily be provided by hand.

I claim:

1. A method for manufacturing a dental prosthesis comprising, establishing the shape of the prepared part of the teeth in question by scanning at least a part of the teeth upon which said dental prosthesis will be applied by means of a three dimensional scanner, establishing a preparation line to form the boundary between the prepared part and the non-prepared part of the teeth by applying a coating which the scanner is capable of recognizing to enable said scanner to establish the location of said preparation line.

2. A method according to claim 1 wherein the said coating is applied on the area of the part of the teeth which is not to be covered by the prosthesis.

3. A method according to claim 1 or 2 wherein said coating includes a colorant.

4. A method according to claim 1 or 2 wherein said scanner detects the surface of the shape to be scanned by means of reflection of a light beam and wherein said coating includes a colorant which absorbs said beam.

5. A method according to claim 1 or 2 wherein said scanner detects the surface of the shape to be scanned by means of reflection of a laser beam and wherein said coating includes a colorant which absorbs said light beam.

6. A method according to claim 1 or 2 wherein said scanner detects the surface of the shape to be scanned by means of reflection of an infrared light beam and wherein said coating includes a colorant which absorbs said laser beam.

7. A method according to claim 1 or 2 wherein coating is black.

8. A method for manufacturing a dental prosthesis comprising, establishing the shape of the prepared part of the teeth in question by scanning a replica of at least a part of the teeth upon which said dental prosthesis will be applied by means if a three dimensional scanner, establishing a preparation line to form the boundary between the prepared part and the non-prepared part of the teeth by applying a coating which the scanner is capable of recognizing to enable said scanner to establish the location of said preparation line.

9. A method according to claim 14 wherein the said coating is applied on the area of the replica of the part of the teeth which is not to be covered by the prosthesis.

10. A method according to claim 8 or 9 wherein said coating includes a colorant.

11. A method according to claim 8 or 9 wherein said scanner detects the surface of the shape to be scanned by means of reflection of a light beam and wherein said coating includes a colorant which absorbs said light beam.

12. A method according to claim 8 or 9 wherein said scanner detects the surface of the shape to be scanned by means of reflection of a laser beam and wherein said coating includes a colorant which absorbs said laser beam.

13. A method according to claim 8 or 9 wherein said scanner detects the surface of the shape to be scanned by means of reflection of an infrared light beam and wherein said coating includes a colorant which absorbs said light beam.

14. A method according to claim 8 or 9 wherein said coating is black.

* * * * *

UNITED STATES PATENT AND TRADEMARK OFFICE
CERTIFICATE OF CORRECTION

PATENT NO. : 5,266,030

DATED : November 30, 1993

INVENTOR(S) : Joseph M. Van Der Zel

It is certified that error appears in the above-identified patent and that said Letters Patent is hereby corrected as shown below:

In claim 9, at column 4, line 27, after "claim" delete "14" and insert --8--.

Signed and Sealed this

Third Day of May, 1994

Attest:

Attesting Officer

BRUCE LEHMAN

Commissioner of Patents and Trademarks